United States Patent

Isak et al.

Patent Number: 5,780,665
Date of Patent: Jul. 14, 1998

[54] PREPARATION OF HALOMETHYLBENZOYL CYANIDES

[75] Inventors: Heinz Isak, Böhl-Iggelheim; Michael Keil, Freinsheim; Bernd Wolf, Fussgönheim; Horst Wingert, Mannheim; Thomas Wettling, Limburgerhof, all of Germany

[73] Assignee: BASF Aktiengesellschaft, Ludwigshafen, Germany

[21] Appl. No.: 836,209

[22] PCT Filed: Nov. 14, 1995

[86] PCT No.: PCT/EP95/04463

§ 371 Date: May 6, 1997

§ 102(e) Date: May 6, 1997

[87] PCT Pub. No.: WO96/16023

PCT Pub. Date: May 30, 1996

[30] Foreign Application Priority Data

Nov. 24, 1994 [DE] Germany ............ 44 41 824.8

[51] Int. Cl.$^6$ ............ C07C 253/14; C07C 253/30
[52] U.S. Cl. ............ 558/342; 558/351; 562/869
[58] Field of Search ............ 562/869; 558/342, 558/351

[56] References Cited

U.S. PATENT DOCUMENTS

| | | | |
|---|---|---|---|
| 4,455,264 | 6/1984 | Findeisen et al. | 260/545 R |
| 4,829,085 | 5/1989 | Wenderoth et al. | 514/522 |
| 5,221,762 | 6/1993 | Wingert et al. | 560/35 |
| 5,352,826 | 10/1994 | Devic et al. | 562/869 |
| 5,446,199 | 8/1995 | Isak et al. | 562/869 |

FOREIGN PATENT DOCUMENTS

| | | |
|---|---|---|
| 70 004 | 5/1983 | European Pat. Off. |
| 254 426 | 1/1988 | European Pat. Off. |
| 352 543 | 1/1990 | European Pat. Off. |
| 398 782 | 11/1990 | European Pat. Off. |
| 28 35 440 | 2/1980 | Germany . |
| 40 42 271 | 7/1992 | Germany . |
| 40 42 272 | 7/1992 | Germany . |
| 40 42 282 | 7/1992 | Germany . |
| 43 11 722 | 4/1994 | Germany . |

OTHER PUBLICATIONS

Jerry March, Adv. Org. Chem. 4th Ed. 1992, pp. 539–552.
A.J. Parker, Chem. Rev. 69, 1–32 (1969).

*Primary Examiner*—Johann Richter
*Assistant Examiner*—Jane C. Oswecki
*Attorney, Agent, or Firm*—Keil & Weinkauf

[57] ABSTRACT

Halomethylbenzoyl cyanides I $$PH-CO-CN \qquad (I)$$

where Ph is phenyl which is substituted by chloromethyl or bromomethyl and may cary 1–4 other rradicals, are prepared from halomethylbenzoyl chlorides II $$PH-CO-Cl \qquad (II),$$

by reacting II with a cyanide-donating compound in the presence of a Lewis acid, if required in an inert organic solvent or diluent, and then isolating the product.

The halomethylbenzoyl cyanides I are important intermediates for synthesizing crop protection agents.

8 Claims, No Drawings

PREPARATION OF HALOMETHYLBENZOYL CYANIDES

This application is a 371 of PCT/EP95/04463 filed on Nov. 14, 1995.

The present invention relates to an improved process for preparing halomethylbenzoyl cyanides of the general formula I

PH—CO—CN     (I)

where PH is phenyl which is substituted by chloromethyl or bromomethyl and which can, if required, also carry from 1 to 4 further radicals which are inert in the reaction, from halomethylbenzoyl chlorides of the general formula II

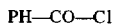

PH—CO—Cl     (II).

DE-C 43 11 722 has disclosed that 2-halomethylbenzoyl chlorides II can be converted by reaction with alkali metal or transition metal cyanides into the corresponding 2-halomethylbenzoyl cyanides I, and that the progress of the process can be beneficially influenced by adding a catalyst. Catalysts said to be suitable are the halides, cyanides, hydroxides, bisulfates, $C_1$–$C_4$-alkyl sulfates and tetrafluoroborates of quaternary nitrogen compounds, and aryl- and alkylphosphonium halides. However, the reactions indicated in the examples reveal that the yields are not entirely satisfactory for a reaction on the industrial scale.

It is an object of the present invention to remedy this deficiency.

We have found that this object is achieved by the present improved process for preparing the halomethylbenzoyl cyanides I, which comprises reacting II with a cyanide-donating compound in the presence of a Lewis acid, if required in an inert organic solvent or diluent, and then isolating the product.

The halomethylbenzoyl chlorides II can be prepared by known halogenation methods from the corresponding methyl-substituted benzene derivatives (for example, DE-A 28 35 440) or from the corresponding benzoic acids (for example, DE-A 40 42 282).

The process according to the invention is normally carried out under atmospheric pressure or slightly reduced pressure, generally at from −20° to 100° C., preferably 0° to 80° C., in particular 20° to 80° C.

Cyanide-donating compounds are, preferably, hydrogen cyanide, cyanohydrin, alkali metal cyanides such as sodium and potassium cyanides or transition metal cyanides such as mercury(I) cyanide, silver cyanide and copper(I) cyanide. Sodium cyanide is particularly expedient.

In general, the halomethylbenzoyl chloride II and the cyanide-donating compound are used in approximately stoichiometric amounts. However, an excess of cyanide, up to a 2-fold quantity, in particular a 1.05–1.5-fold quantity, based on the amount of II, is preferred.

Concerning the use of Lewis acids, reference may be made to Jerry March, Advanced Organic Chemistry, Fourth Edition 1992, pages 539–552, and the literature cited therein.

According to findings to date, particularly particularly suitable catalysts are tin tetrachloride, aluminum chloride, iron(II) chloride, iron(III) chloride, zinc chloride, titanium tetrachloride, boron trifluoride and antimony pentachloride, and tin tetrachloride and titanium tetrachloride are very particularly suitable.

The catalyst is preferably used in amounts of from 0.01 to 5 mol %, in particular from 0.1 to 3 mol %, based on the amount of II.

Where the halomethylbenzoyl chloride II is not in liquid form, it is advisable to add an inert organic solvent or diluent, in which case aprotic dipolar and non-polar solvents are particularly suitable.

Aprotic dipolar solvents are solvents in which a solvent molecule has a pronounced dipole moment but carries no hydrogen atoms capable of hydrogen bonding. The dielectric constant of such solvents is-greater than 15. Concerning the definition of aprotic dipolar solvents, reference may be made to A. J. Parker, Chem. Rev. 69 (1969), 1–32, especially page 2.

Examples of suitable aprotic dipolar solvents are sulfoxides such as dimethyl sulfoxide, diethyl sulfoxide, dimethyl sulfone, diethyl sulfone, methyl ethyl sulfone and tetramethylene sulfone; nitriles such as acetonitrile, benzonitrile, butyronitrile, isobutyronitrile and m-chlorobenzonitrile; N,N-dialkyl-substituted carboxamides such as dimethylformamide, tetramethylurea, N,N-dimethylbenzamide, N,N-dimethylacetamide, N N-dimethylphenylacetamide, N,N-dimethylcyclohexanecarboxamide, N,N-dimethylpropionamide and homologous piperidide, morpholide and pyrrolidide of carboxylic acids, and the corresponding N,N-diethyl, N,N-dipropyl, N,N-diisopropyl, N,N-diisobutyl, N,N-dibenzyl, N,N-diphenyl, N-methyl-N-phenyl, N-cyclohexyl-N-methyl, N-ethyl-N-tert-butyl compounds of the abovementioned N,N-dimethyl compounds, furthermore N-methylformanilide, N-ethylpyrrolidone, N-butylpyrrolidone, N-ethyl-piperidone-(t), N-methylpyrrolidone and hexamethylphosphoric triamide. Mixtures of said solvents are also suitable.

Dimethylacetamide, N-methylpyrrolidone, dimethylformamide, dimethyl sulfoxide, tetramethylene sulfone, acetone and acetonitrile are preferred.

Suitable non-polar solvents are preferably aromatic hydrocarbons such as benzene, toluene and o-, m- and p-xylenes, chlorinated hydrocarbons such as methylene chloride, and alcohols such as methanol and ethanol. Toluene is particularly preferred. The products I can be purified in a conventional way, eg. by distillation.

The process according to the invention can be carried out either batchwise or continuously. In the continuous procedure, the reactants are passed, for example, through a tubular reactor or cascades of stirred vessels. Solvents and catalysts can, if required, be circulated.

The halomethylbenzoyl cyanides I can be obtained by the present process with very good purity and in high yield in a technically straightforward manner. It is normally unnecessary to purify the crude products.

The halomethylbenzoyl cyanides I are valuable intermediates for preparing various crop protection agents, for example the herbicidal 4-phenylpyrazoles described in EP-A 352 543.

The products I can additionally be used to synthesize arylglyoxylic esters as disclosed in DE-A 40 42 271. A mixture of phenylglyoxylic esters and their ketals obtained from the Pinner reaction described therein can be converted as disclosed in DE-A 40 42 272 into the E oxime ethers of phenylglyoxylic esters of the formula III

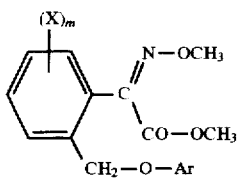

where Ar is substituted or unsubstituted phenyl. Compounds of the type of III are used in crop protection, preferably as fungicides, acaricides or insecticides (for example, EP-A 253 213 and EP-A 254 426).

With a view to the active substances III which can be prepared from the compounds I, Ph is, in particular, the radical

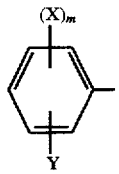

where

X is in each case halogen, especially fluorine or chlorine, $C_1$–$C_4$-alkyl, especially methyl or ethyl, $C_1$–$C_4$-alkoxy, especially methoxy, ethoxy or isopropoxy, $C_1$–$C_4$-haloalkyl, especially trifluoromethyl, —C($C_1$–$C_5$-alkyl)=N—O—($C_1$–$C_5$-alkyl) or —C($C_1$–$C_5$-alkyl)=N—O—($C_2$–$C_5$-alkenyl), in particular methylhydroxylimino or —C(CH$_3$)=N—OCH$_3$;

particularly preferably halogen, $C_1$–$C_4$-alkyl, $C_1$–$C_4$-alkoxy or $C_1$–$C_4$-haloalkyl;

m is from 0 to 4, in particular 1, in which case X is preferably in position 3, 5 or 6, and Y is chloromethyl or bromomethyl, especially chloromethyl, and Y is preferably in position 2.

Ph is very particularly preferably chloromethylphenyl or bromomethylphenyl.

PREPARATION EXAMPLES

Example 1

Preparation of 2-chloromethylbenzoyl cyanide in acetonitrile 7.8 g (3 mol %) of tin tetrachloride are added to a suspension of 196 g (4 mol) of sodium cyanide in 1000 ml of acetonitrile. The mixture was then heated to 60° C. and, over the course of 30 minutes, 378 g (2 mol) of 2-chloromethylbenzoyl chloride were added dropwise. The mixture was stirred at about 60° C. for 6 hours and then cooled. The undissolved catalyst was then removed by filtration through silica gel. Alternatively, the catalyst can also be washed out of the reaction mixture after adding toluene using 200 ml of a dilute mineral acid three times.

The clear solution remaining after removal of the catalyst was subjected to fractional distillation. Yield: 345.8 g (97%); boiling point (0.5)=105° C.

Example 2

Preparation of 2-chloromethylbenzoyl cyanide in toluene

The preparation took place as in Example 1 but using 1000 ml of toluene which contained up to 200 ml of acetonitrile and, after the addition of the 2-chloromethylbenzoyl chloride, stirring for 8 hours. Yield: 317.3 g (89%); boiling point (0.3)=100° C.

We claim:

1. A process for preparing halomethylbenzoyl cyanides of the formula I

Ph—CO—CN            (I)

where PH is phenyl which is substituted by chloromethyl or bromomethyl and which may carry from 1 to 4 further radicals which are inert in the reaction, from halobenzoyl chlorides of the formula II Ph—CO—Cl            (II)

wherein II is reacted with a cyanide-donating compound in the presence of a Lewis acid.

2. The process of claim 1, wherein the variable Ph is the radical

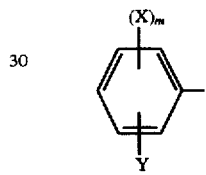

where

X is halogen, $C_1$–$C_4$-alkyl, $C_1$–$C_4$-alkoxy, $C_1$–$C_4$-haloalkyl, —C($C_1$–$C_5$-alkyl)=N—O—($C_1$–$C_5$-alkyl) or —C($C_1$–$C_5$-alkyl)=N—O—($C_2$–$C_5$-alkenyl);

m is 0 to 4, and

Y is chloromethyl or bromomethyl.

3. The process of claim 1, wherein the cyanide-donating compound is an alkali metal cyanide, transition metal cyanide, cyanohydrin or hydrogen cyanide.

4. The process of claim 1, wherein the reaction is carried out in an inert solvent or diluent.

5. The process of claim 1, wherein the reaction is carried out at from −20° C. to 100° C.

6. The process of claim 1, wherein the cyanide-donating compound is used in from approximately stoichiometric amounts up to a 2-fold quantity, based on the amount of II.

7. The process of claim 1, wherein the Lewis acid is used in an amount of from 0.01 to 5 mol-%, based on the amount of II.

8. The process of claim 1, further comprising the isolation of the cyanides of the formula I.

* * * * *